(12) United States Patent  
Amblard

(10) Patent No.: US 7,797,045 B2  
(45) Date of Patent: Sep. 14, 2010

(54) MANAGEMENT OF MODE SWITCHING FOR AN AAI/DDD TYPE IMPLANTABLE DEVICE IN THE PRESENCE OF VENTRICULAR EVENTS OF UNCERTAIN NATURE

(75) Inventor: Amel Amblard, Chatenay-Malabry (FR)

(73) Assignee: ELA Medical S.A.S., Montrouge (FR)

( * ) Notice: Subject to any disclaimer, the term of this patent is extended or adjusted under 35 U.S.C. 154(b) by 480 days.

(21) Appl. No.: 11/423,117

(22) Filed: Jun. 8, 2006

(65) Prior Publication Data

US 2007/0135850 A1    Jun. 14, 2007

(30) Foreign Application Priority Data

Jun. 9, 2005    (FR) .................................. 05 05852

(51) Int. Cl.  
*A61N 1/37*    (2006.01)

(52) U.S. Cl. ........................................................ 607/9

(58) Field of Classification Search .................... 607/9  
See application file for complete search history.

(56) References Cited

U.S. PATENT DOCUMENTS

| 5,318,594 | A | | 6/1994 | Limousin et al. ................ 607/9 |
| 5,379,776 | A | * | 1/1995 | Murphy et al. ............... 600/518 |
| 5,978,708 | A | | 11/1999 | Bonnet et al. .................. 607/14 |
| 2004/0010292 | A1 | | 1/2004 | Amblard .......................... 607/9 |
| 2004/0133245 | A1 | * | 7/2004 | Norn .............................. 607/9 |
| 2005/0240235 | A1 | * | 10/2005 | Limousin et al. ............... 607/9 |

FOREIGN PATENT DOCUMENTS

| EP | 0 488 904 | 4/1995 |
| EP | 0 875 264 | 11/1998 |
| EP | 1 346 750 | 9/2003 |
| EP | 1 470 836 | 10/2004 |

* cited by examiner

*Primary Examiner*—Michael Kahelin  
(74) *Attorney, Agent, or Firm*—Orrick, Herrington & Sutcliffe, LLP

(57) ABSTRACT

An active implantable medical device of AAI/DDD type, notably a cardiac pacemaker, with improved management of mode commutation schemes in the presence of ventricular events of an uncertain nature. The device is able to pace the ventricle and the atrium; sense ventricular events (R, r), apply a safety window following an atrial pacing pulse; perform mode commutation, conditionally triggering commutation of the device from AAI to DDD mode; and diagnose atrio-ventricular conduction disorders determining the appearance of an atrio-ventricular block based upon a sequence of atrial events (A) not followed, during an atrial escape interval, by the detection of the corresponding ventricular event (R) out of the safety window. The device also is able to discriminate ventricular events, detect the occurrence of at least one ventricular event (r) during the safety window, in the absence of a detected atrio-ventricular block, and allowing to trace mode commutation or to inhibit mode commutation if certain conditions are fulfilled.

11 Claims, 1 Drawing Sheet

MANAGEMENT OF MODE SWITCHING FOR AN AAI/DDD TYPE IMPLANTABLE DEVICE IN THE PRESENCE OF VENTRICULAR EVENTS OF UNCERTAIN NATURE

FIELD OF THE INVENTION

The present invention relates to "active implantable medical devices" as such devices are defined by the Jun. 20, 1990 Directive 90/385/CEE of the Counsel of the European Community, and more particularly to single chamber, dual chamber or "multisite" (triple or quadruple chamber) pacemakers, defibrillators and/or cardioverter devices that are able to monitor heart activity and to deliver to the heart electrical pulses intended to achieve pacing, resynchronization, cardioversion and/or defibrillation in response to a diagnosed rhythm disorder.

BACKGROUND OF THE INVENTION

Devices are known that are equipped with pacing and sensing circuits associated with the atrium and the ventricle, that can operate according to two known operating modes, DDD or AAI (the AAI mode being a DDD mode having a lengthened atrio-ventricular delay). These devices may be equipped with a mode called "DDD-AMC" or "AAISafeR", ensuring an automatic mode commutation (switching) from DDD to AAI and conversely. The basic operating mode of a DDD/AAI pacemaker is an AAI mode—or more precisely a "pseudo-AAI" mode—with a single chamber atrial pacing (AAI mode stricto sensu), and a monitoring of ventricular activity. This operating mode is maintained as long as atrio-ventricular conduction is normal, that is, as long as each atrial event (either an atrial detection, corresponding to a spontaneous activity, or an atrial stimulation, corresponding to a paced event) is followed by an associated ventricular detection.

In certain circumstances, however, atrio-ventricular blocks ("AV blocks" or "AVB") may appear, leading to a temporary disorder of depolarization of the ventricle. In this case, as long as several conditions are met, the pacemaker automatically commutes to an automatic DDD mode, with parameters that are optimized for this situation of a temporary AV block. After the disappearance of the AVB, there is a re-establishment of atrio-ventricular conduction, and the pacemaker automatically commutes back to AAI mode, as long as several other conditions are met. Such a commutation between DDD and AAI operating modes, is notably described in EP-A-0488904 and its counterpart U.S. Pat. No. 5,318,594 (commonly assigned herewith to ELA Medical), and EP-A-1346750 and its counterpart U.S. published application 2004/010292 (commonly assigned herewith to ELA Medical).

The present invention is based upon some observations that have been made while actually following-up patients implanted with DDD/AAI pacemakers with the aforementioned known automatic mode commutation features. Indeed, it has been observed that such devices provide an insufficient specificity for sensing ventricular disorders, such that, in some cases, there are inappropriate mode commutations towards the DDD mode. Indeed, the basic principle for such a device is that when it is operating in AAI mode, any ventricular detection maintains the device in AAI mode (i.e., inhibits commutation to DDD mode), except when such conditions permit a suspicion of an AVB appearance.

The device considers there is an AVB when several criteria are met, revealing a conduction that is actual, but delayed (first degree AVB), or some P-waves that are no longer conducted (second degree AVB), or that are totally blocked (complete, or third degree AVB).

Commuting to DDD mode also can be triggered by the diagnosis of a ventricular pause, i.e., when the interval between two consecutive ventricular events is longer than a specified delay. Detection of a spontaneous ventricular depolarization, and the calculation of the time interval since the previous atrial event, are therefore essential in the diagnosis of AVB, and thus for determining potential commuting to DDD mode.

Notably, after delivering an atrial pacing pulse, the device applies to the sensing circuit, a period called "safety window", typically 100 ms after an atrial pacing pulse such that if a depolarization is detected before the end of the safety window, it is not taken into account by the device; indeed, due to the very short delay separating this sensing from the previous atrial pacing, it could likely be confused with the sensing of an electric artifact, associated with the recovery time of sensing amplifier for instance. For this reason, in the devices well known in the art, such a depolarization is systematically ignored and is not considered as the end (or beginning) of a ventricular cycle, notably for the management of various intervals (escape interval, atrio-ventricular delay) and management of potential commutation from AAI mode to DDD mode.

But, in some cases, such sensing can be related to an actual ventricular activity, the short AV delay being possibly explained by:

Either a systemic dysfunction, notably consecutive to a defect in sensing a spontaneous atrial event, or a true atrio-ventricular asynchrony: pathologic lengthening of AV delay, junctional rhythm, chronotropic incompetence with acceleration of ventricular rhythm, etc.

In the absence of any verification of the true nature of the sensed event within the safety window, the device considers, as a safety measure, that there is an atrio-ventricular defect, in such a way that occurrence of several events of this type may lead to commuting to DDD mode.

Hence, other than the non-detection of a potential ventricular disorder that would be responsible for this situation, the device operation is modified by a false diagnosis leading to an inappropriate commutation to DDD mode. Though DDD mode operation commonly has no deleterious effect to the patient, such a commutation is useless and prevents spontaneous atrio-ventricular conduction, and is therefore generally less desirable.

OBJECTS AND BACKGROUND OF THE INVENTION

It is therefore, an object of the present invention to propose a device that allows to characterize phenomena of this type, corresponding to a true ventricular activity and, in the case that a commutation to DDD mode has actually occurred, allows to identify these particular commutations, notably in order to disclose them to a physician later on, in a certain manner so as to distinguish them from commutations associated with a confirmed conduction disorder.

It is another object of the present invention to propose a device that, beyond characterization of these phenomena, is able to adapt the automatic mode commutation so as to prevent an inappropriate commutation to DDD mode in these particular cases thus identified.

The type of device to which the invention applies is a known device of "AAISafeR" type, for example following EP-A-0488904 or EP-A-1346750 or their U.S. counterparts referred to above, including: means for pacing the ventricle and the atrium, means for sensing atrial events, operating with the control of a safety window following the delivery of an atrial pacing pulse; means to allow the device to operate in AAI mode with ventricular sensing, or in DDD mode; means for performing mode commutation, able to conditionally schedule commutation from AAI to DDD mode; and means for diagnosing atrio-ventricular conduction disorders, able to determine the appearance of an AV block, based upon a sequence of atrial events that are not followed, throughout the duration of an atrial escape interval, by sensing of the corresponding ventricular event out of the safety window.

In a preferred embodiment, the device also includes means for discriminating ventricular events, able to detect the occurrence of at least one ventricular event during the safety window, in the absence of AV block detected by the means of diagnosis of conduction disorder.

When the means of diagnosis of atrio-ventricular conduction disorder triggers a commutation from AAI to DDD mode, in case of commutation, the means for discriminating ventricular events can position and associate a first event marker to that mode commutation, this first marker being representative of a commutation that is not related to an AV block. Likewise, they can position and associate a second event marker to the episode that began on the commutation with which the first marker is associated, that second marker being representative of an episode that is not related to an AV block. These markers can notably be subjected to counting for statistical purposes.

Advantageously, the means for discriminating ventricular events can inhibit, as a function of predetermined criteria, the commutation from AAI to DDD mode. Such criteria can be based upon the detection of the shortening of AV delay over a first predetermined number of cycles preceding the detection of said event during the safety window, concurrently with the detection of a stable atrial rhythm. Or these criteria can be based upon the detection of a second predetermined number of cycles, in which the AV delay is longer than atrial coupling interval by a given duration or proportion of duration.

Additionally, in order to try and identify the ventricular event during the safety window, the means for discriminating ventricular events can modify the atrial escape interval duration after sensing said ventricular event during the safety win-dow, or even temporarily cancel atrial pacing.

BRIEF DESCRIPTION OF THE DRAWINGS

Further features, advantages and characteristics of the present invention will become apparent to a person of ordinary skill in the art when considered in view of the following detailed description of a preferred embodiment of the invention, made with reference to the drawings annexed hereto, in which.

DETAILED DESCRIPTION OF THE INVENTION

One now will describe an exemplary embodiment of a device in accordance with a preferred embodiment of the invention.

Regarding the software-related aspects thereof, the present invention can be implemented by means of an appropriate programming of the software of a known active implantable device, for example, of the pacemaker type, or defibrillator/cardioverter type, including means for acquiring a signal conveyed by endocardial leads and/or several implanted sensors. The invention can notably be applied to the implantable devices marketed by ELA Medical, Montrouge, France, such as the Symphony and Rhapsody brand pacemakers, and the Alto and Ovatio brand defibrillators. These devices are equipped with programmable microprocessors, including circuits intended to acquire, format and process electrical signals collected by implanted electrodes, and deliver pacing pulses to these electrodes. It is also possible to upload towards these devices, by telemetry, pieces of software that will be stored in internal memory and run so as to implement the features of the invention, described in more detail below. Implementing the features of the invention into these devices is easily feasible by the person of ordinary skill in the art, and will therefore not be described in detail in this document.

Figure 1:
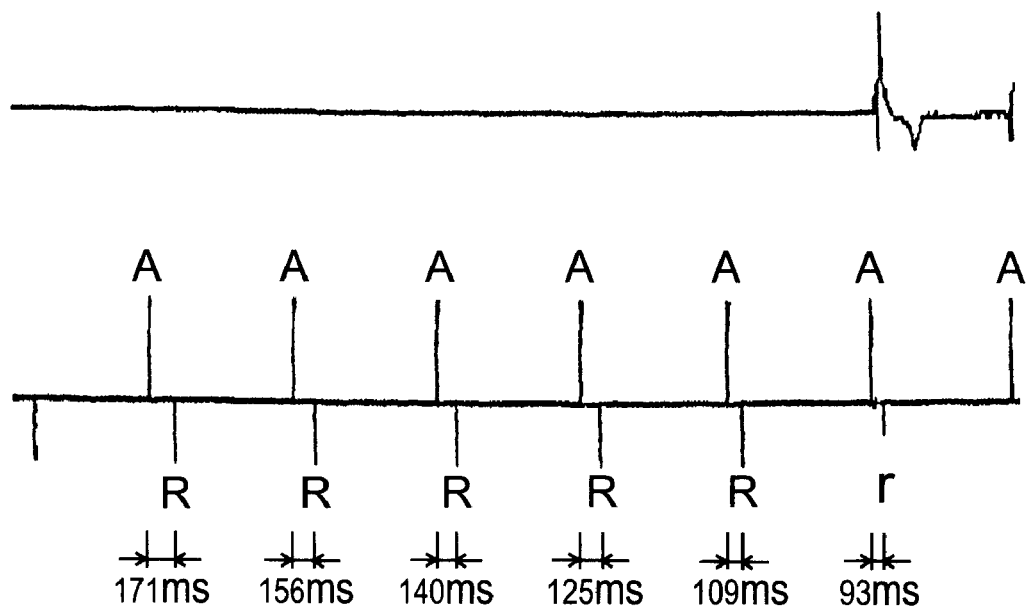
FIGS. 1 and 2 are timing diagrams showing two situations when particular ventricular events occur and are detected in conformance with the present invention.

With reference to FIG. 1, event markers A show the time position of consecutive atrial pacing pulses, typical of AAI mode operation. In case of normal atrio-ventricular conduction, i.e., in the absence of AVB, the device senses, after each pacing pulse, an associated ventricular depolarization (R wave).

After delivering a pacing pulse A, the device applies to the sensing circuit, a period called "safety window", that has a duration of typically 100 ms following the atrial pacing pulse. Other time periods also may be used, e.g., from 30 to 150 ms. This window is applied such that if a depolarization is detected before the end of the safety window, it will be ignored by the device, for in this case, provided the detected event is deemed close to the previous atrial pacing pulse, its nature is uncertain: it can notably present the detection of an electric artifact, related for example to the recovery time of the ventricular sensing amplifier, or an isolated ventricular extrasystole, which are phenomena that could interfere with the normal operation of heart rhythm analysis algorithm. But in certain particular cases, this ventricular detection during the safety window can reveal a true ventricular activity.

Short AR delay can then be justified by either a systemic dysfunction (loss of atrial sensing), or a true atrio-ventricular asynchrony: notably, pathologic lengthening of atrio-ventricular delay, junctional rhythm or chronotropic incompetence with acceleration of the ventricle.

The devices of the prior art, as a safety measure, do consider that an atrial pacing pulse followed by a ventricular sensing R during the safety window, is to be correlated to an AV block, in such a way that occurrence of several events of this type may lead to commutation to DDD mode.

A first embodiment of the invention therefore proposes to characterize the commutations related to such phenomena, so as to associate thereto, specific markers that can be disclosed to a physician later on, when reading the recording of data performed by the device, and in such a way that these commutations are distinguished from those associated with a confirmed AV conduction disorder.

To that end, each time a commutation occurs, for which the last ventricular cycle presents an atrial pacing pulse followed by a ventricular detection during the safety window, the device associates to this commutation, a specific marker representative of a "commutation not related to an AVB". Likewise, each episode starting with such a "commutation not related to an AVB" will be associated with a specific marker representative of an "episode not related to an AVB". An "episode" is a succession of cycles starting from a commutation from AAI to DDD mode, and ending for example, after a pre-selected number, e.g., 100, of consecutive cycles in DDD mode with no commutation back to AAI mode (the device will then be able to force commutation back to AAI mode if certain conditions are fulfilled, in order to improve potential spontaneous AV conduction to occur).

The commutations and episodes "not related to an AVB" are respectfully documented by specific markers, subjected to specific statistics, and associated with a corresponding electrogram ("EGM") recording for the particular cycle during which commutation has been triggered.

A second embodiment of the invention proposes to adapt automatic mode commutation in such a manner so as to prevent, in certain cases, from commutating to DDD mode when that mode is not appropriate.

The first case, corresponding to the chronogram on FIG. 1, is a case in which the detection during the safety window (event referred to as "r", distinguished from the events detected out of the safety window, referred to as "R") is preceded by a shortening of AR delay over a certain number of preceding cycles, while in the presence of a stable atrial rhythm. Thus one can see on FIG. 1 that the AR interval takes successive decreasing values: 171, 156 ... 109, 93 ms, in such a way that the last "r" event, AR interval of which is 93 ms, occurs within the 100-ms safety window. In such a situation, the algorithm suspects a chronotropic incompetence with ventricular acceleration, and inhibits the commutation towards DDD mode, that would otherwise have been triggered by a device of the prior art.

Figure 2:
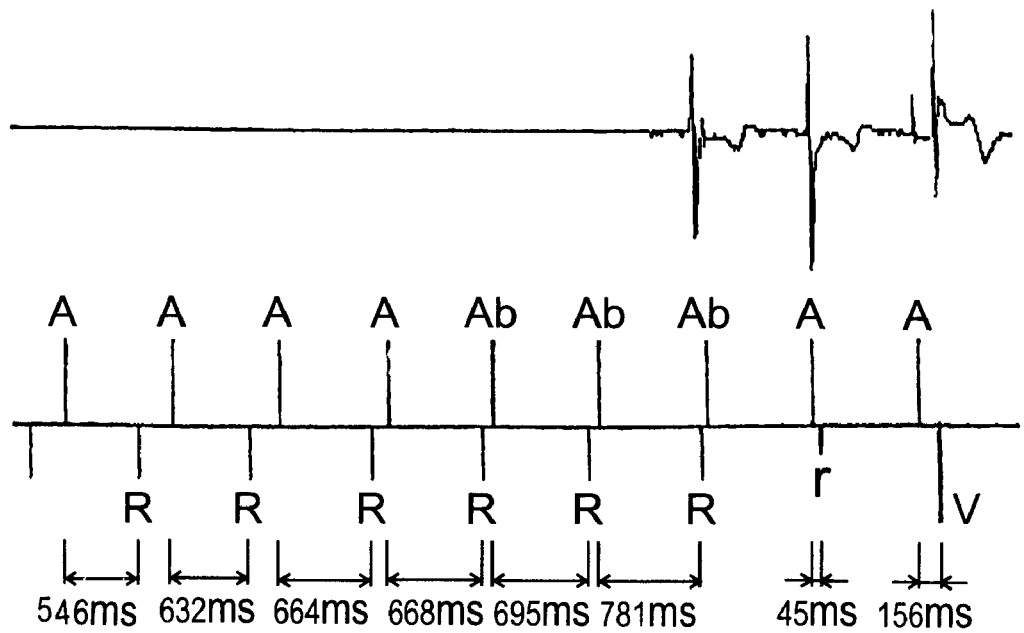

Another case is illustrated by FIG. 2, conversely presenting a progressive lengthening of AR interval, such that this interval gets to exceed the atrial coupling interval (AA interval), and finally falls right into the safety window of the following atrial pacing. More precisely, the device considers itself to be in the presence of such a situation, if the "r" detection during the safety window is preceded by a certain number of cycles (not necessarily consecutive), for which the ratio between AR interval and RR interval, is higher than a given percentage, for example, 75% (the analysis can alternatively or in addition be based upon the ratio AR interval/AA interval).

Yet, another embodiment of the present invention proposes to modify the control algorithm of the device, so as to allow the ventricular detections during the safety window to re-occur. That modification aims at preventing commutations in response to events of this type, by trying to identify a potential ventricular activity.

Thus, for each atrial pacing pulse followed by a detection during the safety window, it is notably possible to:
   shorten the atrial escape interval by a parameterizable delay, or
   lengthen the atrial escape interval by a parameterizable delay, or
   suspend atrial pacing.

If one of these modifications reveals an identified ventricular activity, then the corresponding atrial pacing is not considered as being related to an AV block.

One skilled in the art will appreciate that the present invention can be practiced by other than the described embodiments, which are presented for purposes of illustration and not of limitation.

I claim:

1. An active implantable medical device of a cardiac pacemaker, defibrillator and/or cardioverter type, comprising:
   means for pacing the ventricle and atrium;
   means for detecting atrial events (A);
   means for detecting ventricular events (R, r), operating with the application of a safety window following the delivery of an atrial pacing pulse;
   means for operating the device in AAI mode with ventricular sensing, or in DDD mode;
   means for mode commutation conditionally performing commutation from AAI to DDD mode;
   means for diagnosing an atrio-ventricular conduction disorder by determining the appearance of an atrio-ventricular block based upon a sequence of atrial events (A) not followed, during one atrial escape interval, by the detection of a corresponding ventricular event (R) out of said safety window;
   means for discriminating ventricular events by detecting the occurrence of at least one ventricular event (r) during the safety window, in the absence of an atrio-ventricular block detected by said means for diagnosing an atrio-ventricular conduction disorder, wherein said means for discriminating ventricular events comprises means for placing in a timing diagram event markers representative of the atrial events and the ventricular events, the means for placing event markers, in case of mode commutation from AAI to DDD mode in the absence of the atrio-ventricular block, positioning a first marker in the timing diagram and associating the first marker to said mode commutation, said first marker being representative of a commutation from AAI mode to DDD mode not related to an atrio-ventricular block; and
   a memory storing an electrogram (EGM) during a cycle associated with the first marker.

2. The device of claim 1 further comprising means for counting the number of said first markers.

3. The device of claim 1, wherein:
   said means for the mode commutation further comprises means, after commutation from AAI to DDD mode, for maintaining the device in DDD mode during a predetermined episode duration, and
   said means for discriminating ventricular events further comprises means for positioning and associating a second marker to the episode that has begun on the commutation associated with said first marker, said second marker being representative of an episode not related to an atrio-ventricular block.

4. The device of claim 3 further comprising means for counting the number of said first and/or second markers.

5. The device of claim 1, wherein means for discriminating ventricular events further comprises means for inhibiting commutation from AAI to DDD mode as a function of a predetermined criteria.

6. The device of claim 5, wherein said means for discriminating ventricular events further comprises means for inhibiting commutation from AAI to DDD mode in case of detection of, concurrently: a progressive shortening of atrio-ventricular delay over a first predetermined number of cycles preceding the detection of said ventricular event during the safety window; and a stable atrial rhythm.

7. The device of claim 5, wherein said means for discriminating ventricular events comprises means for inhibiting commutation from AAI to DDD mode in the case of detection of a second predetermined number of cycles for which the atrio-ventricular delay gets longer than the atrial coupling interval by a given duration or proportion of duration.

8. The device of claim 1, wherein said means for discriminating ventricular events further comprises means for modifying the duration of the atrial escape interval after the detection of said ventricular event during the safety window.

9. The device of claim 1, wherein said means for discriminating ventricular events further comprises means for suspending atrial pacing after the detection of said ventricular event during the safety window.

10. The device of claim 1 further comprising means for detecting a stable atrial rhythm.

11. The device of claim 1 further comprising means for shortening said atrio-ventricular delay over a first predetermined number of cycles preceding the detection of said ventricular event during the safety window.

* * * * *